(12) United States Patent
Eckert et al.

(10) Patent No.: US 9,909,849 B2
(45) Date of Patent: Mar. 6, 2018

(54) METHOD AND SYSTEM FOR MEASURING MEDICATION AND AUTOMATIC LOADING OF A DATABASE

(71) Applicant: Aesynt Incorporated, Cranberry Township, PA (US)

(72) Inventors: Robert Eckert, Eighty Four, PA (US); Kirk Young, Pittsburgh, PA (US)

(73) Assignee: Aesynt Incorporated, Cranberry Township, PA (US)

( * ) Notice: Subject to any disclaimer, the term of this patent is extended or adjusted under 35 U.S.C. 154(b) by 528 days.

(21) Appl. No.: 14/599,785

(22) Filed: Jan. 19, 2015

(65) Prior Publication Data

US 2016/0206514 A1     Jul. 21, 2016

(51) Int. Cl.
| | | |
|---|---|---|
| G01B 21/00 | (2006.01) | |
| G01B 3/20 | (2006.01) | |
| G06F 19/00 | (2018.01) | |
| A61J 7/00 | (2006.01) | |
| G06T 7/00 | (2017.01) | |

(52) U.S. Cl.
CPC ......... *G01B 3/205* (2013.01); *G06F 19/3462* (2013.01); *A61J 7/00* (2013.01); *G06T 7/0012* (2013.01)

(58) Field of Classification Search
CPC ... G06F 19/3462; G01B 3/205; G06T 7/0012; A61J 7/00

USPC .......................................................... 702/158
See application file for complete search history.

(56) References Cited

U.S. PATENT DOCUMENTS

| | | |
|---|---|---|
| 4,226,024 A | 10/1980 | Westerberg et al. |
| 4,782,448 A | 11/1988 | Milstein |
| RE35,084 E | 11/1995 | Lorenz |
| 6,535,637 B1 | 3/2003 | Wootton et al. |
| 6,658,755 B2 | 12/2003 | Arlinsky |
| 7,765,712 B2 | 8/2010 | Stockman |
| 7,995,831 B2 | 8/2011 | Eller et al. |
| 8,712,163 B1 * | 4/2014 | Osheroff ................... G06K 9/00 382/149 |
| 2009/0138122 A1 | 5/2009 | Wagner |
| 2011/0267450 A1 | 11/2011 | Pronkine |
| 2011/0270525 A1 | 11/2011 | Hunter |

* cited by examiner

*Primary Examiner* — Paul D Lee
(74) *Attorney, Agent, or Firm* — The Webb Law Firm

(57) ABSTRACT

A system and method for measuring medication includes providing a graphical user interface (GUI) including a representation of a medication or a medication container. An indication to measure at least one dimension of the medication or the medication container is provided in the GUI. At least one signal including at least one measured dimension of the medication or the medication container is received by one or more processors that process and store the at least one measured dimension. The at least one measured dimension is provided in the GUI in association with the indication to measure the at least one dimension of the medication or the medication container.

18 Claims, 6 Drawing Sheets

METHOD AND SYSTEM FOR MEASURING MEDICATION AND AUTOMATIC LOADING OF A DATABASE

BACKGROUND OF THE INVENTION

Field of the Invention

This disclosure relates to embodiments of a system, apparatus, and/or method for measuring medication and, in particular, to a method and system for measuring dimensions of a medication and/or a medication container and automatically storing the measurements in a database.

Description of Related Art

In order for medication to be handled by automated systems, measurements of the medication and/or a medication container must be taken. Conventionally, these measurements have been performed manually with mechanical calipers and then loaded into a database by an operator manually keying in the measured values. This is a time consuming process that may result in errors in the measured values as the complexity of the measurements increases. Moreover, the user is not provided with any instruction on which measurements to take or the correct manner of taking the measurements.

U.S. Patent Application Publication No. 2011/0270525 discloses a digital caliper to take measurements of oil and gas equipment. U.S. Pat. No. 6,658,755 discloses a tape measure that digitally displays the current measurement and transmits the measurement to a remote computer. U.S. Pat. No. 4,782,448 is directed to a digital ruler that transmits measurement information via a wireless signal. U.S. Pat. No. 7,765,712 to Stockman is directed to another digital caliper. U.S. Patent Application Publication Nos. 2009/0138122 and 2011/0267450 and U.S. Pat. Nos. 4,226,024, RE 35,084, 6,535,637, 7,995,831 describe various other conventional measuring or imaging systems.

SUMMARY OF THE INVENTION

Generally, provided is a medication measurement system and method that addresses or overcomes some or all of the deficiencies and drawbacks associated with existing medication measurement processes. For example, a system and method are disclosed herein for electronically collecting dimension measurement values of a medication and/or a medication container and a graphical user interface (GUI) for guiding an operator in the collection of the measurement values. Further, a system and method are disclosed herein for automatically storing the measurement values and processing the measurement values to check for errors and/or create derived values therefrom.

According to an aspect of the disclosure, a system for measuring medication may comprise at least one non-transitory computer-readable storage medium in communication with the one or more processors and has instructions stored thereon. The instructions, when executed by the one or more processors, cause the one or more processors to perform operations comprising providing a GUI including a representation of a medication or a medication container; providing in the GUI an indication to measure at least one dimension of the medication or the medication container; receiving at least one signal comprising at least one measured dimension of the medication or the medication container; processing the at least one measured dimension; storing the at least one measured dimension; and providing the at least one measured dimension in the GUI in association with the indication to measure the at least one dimension of the medication or the medication container.

According to another aspect of the disclosure, a method for measuring medication may comprise providing, by one or more processors, the GUI, which includes a representation of a medication or a medication container. An indication is provided in the GUI to measure at least one dimension of the medication or the medication container. At least one signal comprising at least one measured dimension of the medication or the medication container is received by the one or more processors, which process and store the at least one measured dimension. The one or more processors provide the at least one measured dimension in the GUI in association with the indication to measure the at least one dimension of the medication or the medication container.

The indication to measure the at least one dimension of the medication or the medication container may comprise at least one marking in the GUI indicating the dimension on the representation of the medication or the medication container. The at least one marking in the GUI may comprise at least one leader line and at least one arrow.

Processing the at least one measured dimension may comprise determining that the measured dimension fails to satisfy at least one tolerance threshold. The one or more processors may set the at least one tolerance threshold based at least partly on at least one previously measured dimension of the medication or the medication container.

Processing the at least one measured dimension may comprise calculating a derived value based at least partly on the at least one measured dimension and may be based at least partly on at least one previously measured dimension of the medication or the medication container. The derived value may be another dimension of the medication or the medication container.

The one or more processors may receive information indicating a type of the medication or the medication container, and the representation may be based at least partly on the information indicating the type of the medication or the medication container.

Receiving the information may comprise at least one of scanning a barcode on the medication or the medication container and capturing an image of the medication or the medication container.

The system may further comprise a digital caliper. The digital caliper may measure the at least one measured dimension and transmit the at least one measured dimension to the one or more processors via a communications interface.

These and other features and characteristics of certain and non-limiting embodiments, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

BRIEF DESCRIPTION OF THE DRAWINGS

Further features and other objects and advantages will become apparent from the following detailed description made with reference to the drawings in which.

DESCRIPTION OF THE INVENTION

Figure 1:
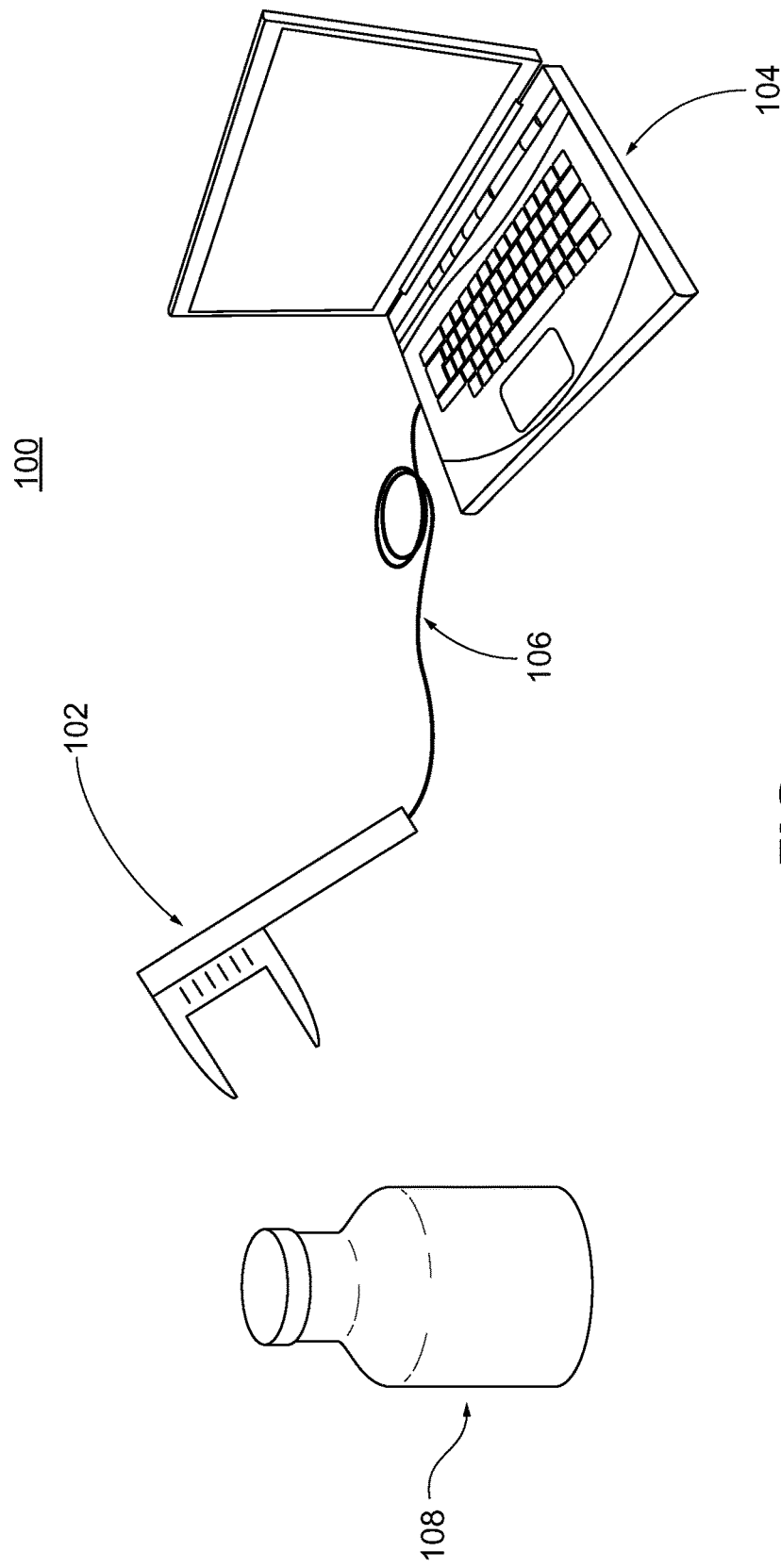
FIG. 1 is a schematic view of a system for measuring medication sizes according to an aspect of the disclosure.

For purposes of the description hereinafter, the terms "end", "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that may be wired and/or wireless in nature. Additionally, two units or components may be in communication with each other even though the data transmitted may be modified, processed, routed, and the like, between the first and second unit or component. For example, a first unit may be in communication with a second unit even though the first unit passively receives data, and does not actively transmit data to the second unit. As another example, a first unit may be in communication with a second unit if an intermediary unit processes data from one unit and transmits processed data to the second unit. It will be appreciated that numerous other arrangements are possible.

Referring to FIG. 1, a system for measuring medication sizes 100 may comprise a digital caliper 102, a computer 104, and a communications interface 106 for communications between the digital caliper 102 and the computer 104. The digital caliper 102 is capable of measuring dimensions of a container 108, e.g., a container holding a medication, and/or directly measuring dimensions of a medication itself, e.g., a solid medication. The container 108 may be a medicine bottle, a pill holder, a vial, a syringe, an IV bag, or any other known medical container for containing a medication in a solid, liquid, and/or gas state.

Although illustrated in FIG. 1 and described herein as a digital caliper, the digital caliper 102 may comprise any electronic tool capable of collecting a dimensional measurement value of an item or object. For example, the digital caliper 102 may comprise a laser scanner configured to determine dimensions of the container 108 based on a scan of the container 108, or an image capture device configured to determine dimensions of the container 108 based on an image of the container 108 using image analysis software.

Figure 2:
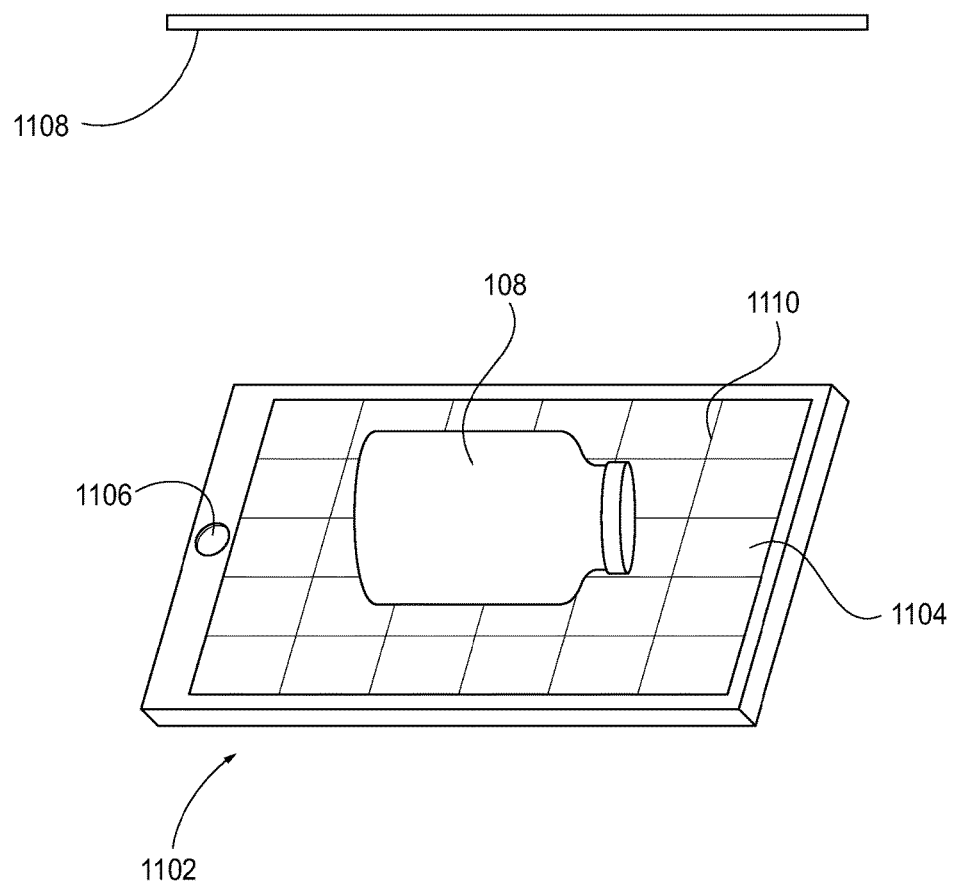
FIG. 2 is a schematic view of a non-limiting embodiment of an image capture device according to an aspect of the disclosure.

In one non-limiting embodiment, depicted in FIG. 2, image capture device can be a smartphone or tablet 1102 having a display screen 1104 and camera 1106. A mirror or other reflective surface 1108 can be positioned opposite the display screen 1104 and configured such that the camera 1106 can capture an image of the display screen 1104 through a reflection from the reflective surface 1108. The image capture device 1102 can have a program running thereon which causes a grid 1110 to be displayed on the screen 1104. The container 108 can be positioned between the display screen 1104 and the reflective surface 1108 so that the container 108 obstructs at least a portion of the screen 1104. The camera 1106 can then be activated to capture an image of the screen 1104 as obstructed by the container 108. The image can be analyzed to determine the dimensions of the container 108 based on the captured image. For example, the dimensions of the container 108 can be determined based, at least in part, by determining what portion of the grid 1110 has been obstructed by the container 108. In another non-limiting embodiment (not shown), a camera can be positioned directly above the display screen 1104, obviating the need for the reflective surface 1108.

The digital caliper 102 may be operated by a user. For example, the user may place the digital caliper 102 on the medication or the container 108 at a desired location and instruct the digital caliper 102 to record a measurement. The digital caliper 102 records a measurement value and automatically transmits the measurement value to the computer 104 via the communications interface 106. Alternatively, the digital caliper 102 may be operated via an automatic or remotely controlled robotic system to measure one or more dimensions of the medication or the container 108. For example, a vision system camera may provide a remote operator or control software controlling the robotic system the ability to control the digital caliper 102 to perform the desired measurements of the medication or the container 108.

Although certain and non-limiting embodiments are discussed herein with respect to a digital caliper, a manual caliper instead of the digital caliper may be used to record the measurement values, and an operator may manually enter measurement values taken with the manual caliper into the computer 104.

The digital caliper 102 may further comprise a sensor configured to determine whether a medication inside the container is a solid, a powder, a liquid, a gel, or a gas.

The communications interface 106 between the digital caliper 102 and the computer 104 may be a wired or wireless interface. For example, the communications interface 106 is shown in FIG. 1 as a USB connection between the digital caliper 102 and the computer 104; however, disclosed embodiments are not limited thereto and the digital caliper 102 and the computer 104 may comprise wireless interface modules for wireless communications, e.g., via Wi-Fi and/or Bluetooth over the Internet or another network. The digital caliper 102 communicates measured values and other information about the medication or container 108 to the computer 104, and the computer 104 may transmit initialization commands, control instructions, and software updates to the digital caliper 102.

Figure 6:
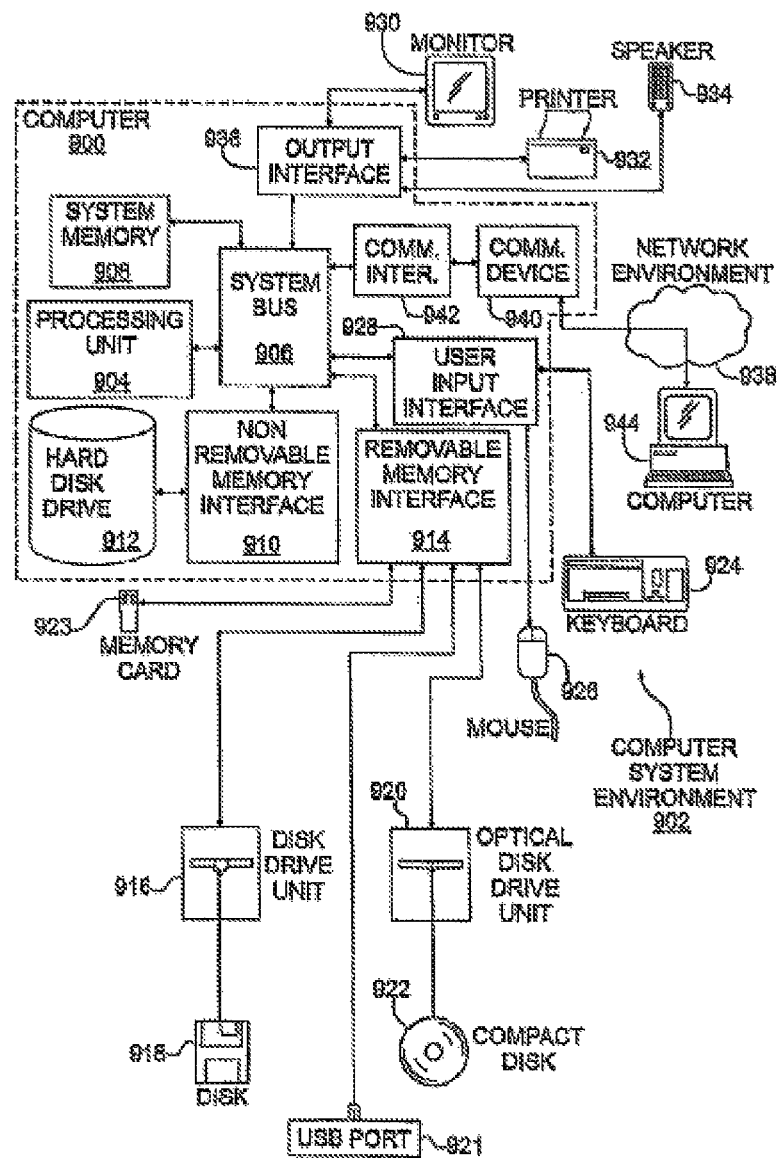
FIG. 6 is a block diagram of an example computer system according to aspects of the disclosure.

The computer 104 may be implemented on a variety of computing devices and systems, wherein these computing devices include the appropriate processing mechanisms and computer-readable media for storing and executing computer-readable instructions, such as programming instructions, code, and the like to provide a graphical user interface on a display. FIG. 6, which is discussed in more detail below, is a block diagram of an exemplary computer system according to this disclosure.

Figure 3:
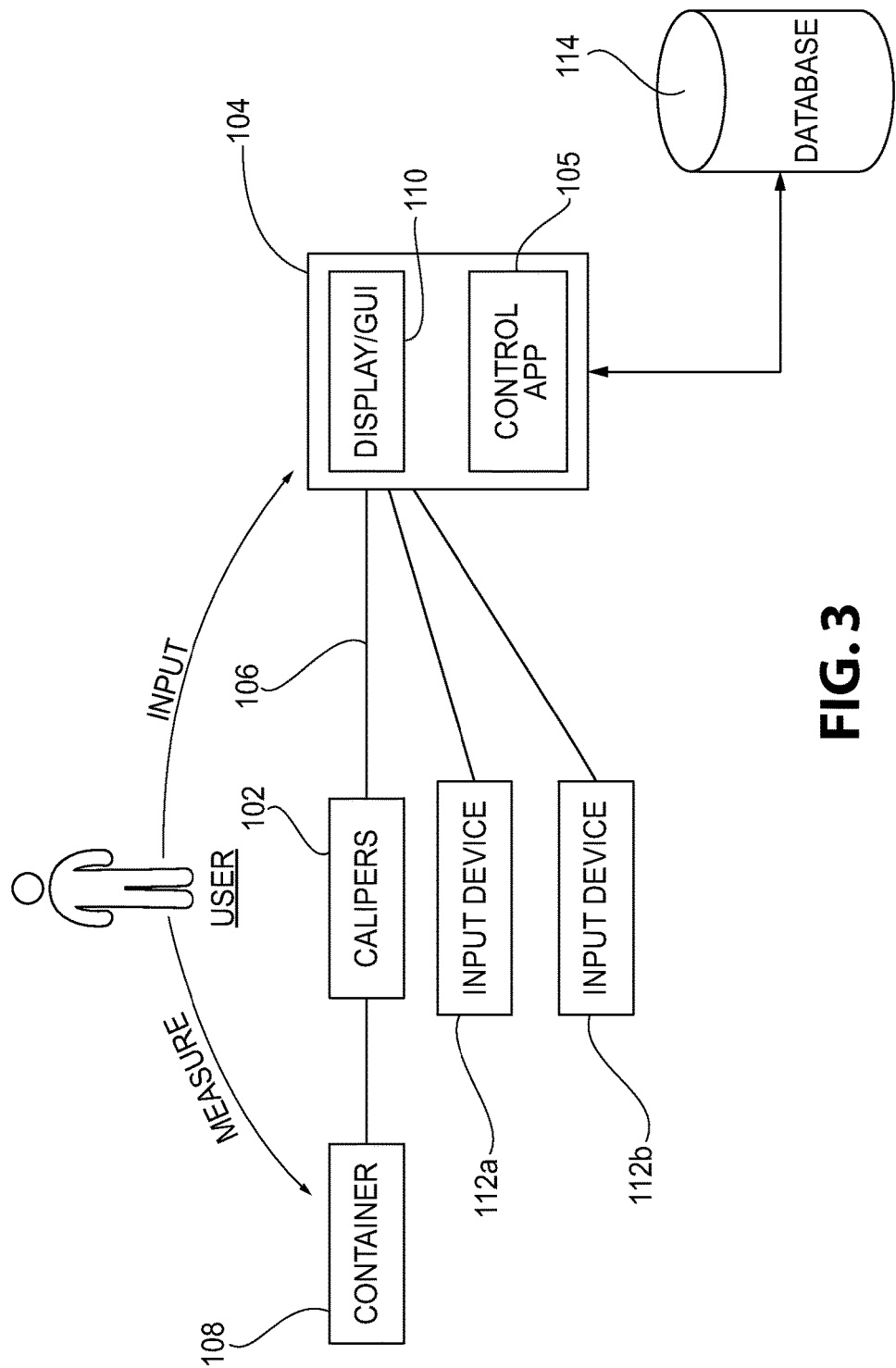
FIG. 3 is a block diagram of modules of a system for measuring medication sizes according to an aspect of the disclosure.

FIG. 3 is a block diagram of modules of a system for measuring medication sizes according to a certain and non-limiting embodiment. The computer 104 comprises a display 110 for displaying a GUI to the user and executing a control application 105 for controlling the system. The computer 104 may be connected to one or more input devices or tools 112a, 112b via various wired or wireless communications interfaces and/or networks, and to the digital caliper 102 via the communications interface 106. For example, the sensor configured to determine the form of the medication inside the container, e.g., whether the medication is a solid, a powder, a liquid, a gel, or a gas, may be a separate sensor from the digital caliper 102, and/or the one or more input devices 112a, 112b may comprise a barcode reader capable of reading a barcode and sending the information contained therein to the computer 104. Alternatively, the digital caliper 102 may comprise the barcode reader. In another certain and non-limiting embodiment, the one or more input devices 112a, 112b may comprise a camera configured to input an image to the computer 104, for example, an image of the medication or the container 108. The computer 104 may further comprise and/or be in communication with a database 114.

The computer 104 may automatically store the measured values received from the digital caliper 102 or manually entered by the user via the display 110 in the database 114. The database 114 stores the measured values in association with an identification number for the medication or container 108. The database 114 may be pre-loaded with or store dimensions and values of known medications or containers 108. For example, containers 108 for which the dimensions are already known without measurement, e.g., that have been provided by the manufacturer, may be stored in the database 114 without first being measured/entered by the user. The database 114 may store instructions associated with particular container types that may be presented to the user via the GUI to aid the user in measuring the container 108. For example, the computer 104 may identify instructions for a container stored in the database 114 that are associated with the container 108 to be measured based on the identification number entered by the user, a name or type of the container entered by the user, or the image of the container received from the camera. Other information, including cost, manufacturer, product date, etc., may also be stored in the database 114 for each container 108 or type of container.

Referring to FIGS. 1-4, FIG. 4 is an example of a display (e.g., GUI) 110 according to a preferred and non-limiting embodiment. The control application 105 controls the display 110 to output the GUI to the user. The GUI provides a representation 302 of the medication or the container 108 to be measured. The representation 302 may be based on information and/or images stored in the database 114. For example, the operator may enter the identification number, a name or type of the medication or the container 108, scan a barcode on the container 108, or upload an image of the medication or container 108 using a camera input device 112a, and the control application 105 may control the GUI to display a representation 302 associated with the input information in the database 114 and/or the actual image from the camera input device 112a.

The GUI accepts a user input of the identification number and displays the identification number with the representation of the medication or the container 108 in an identification number area 304. The GUI provides a type selection panel 306 in which the user selects a representation of the container 108 with or without a cap and selects the type of medication contained or to be contained in the container 108, e.g., liquid, solid, powder, gel, or gas.

Figure 4:
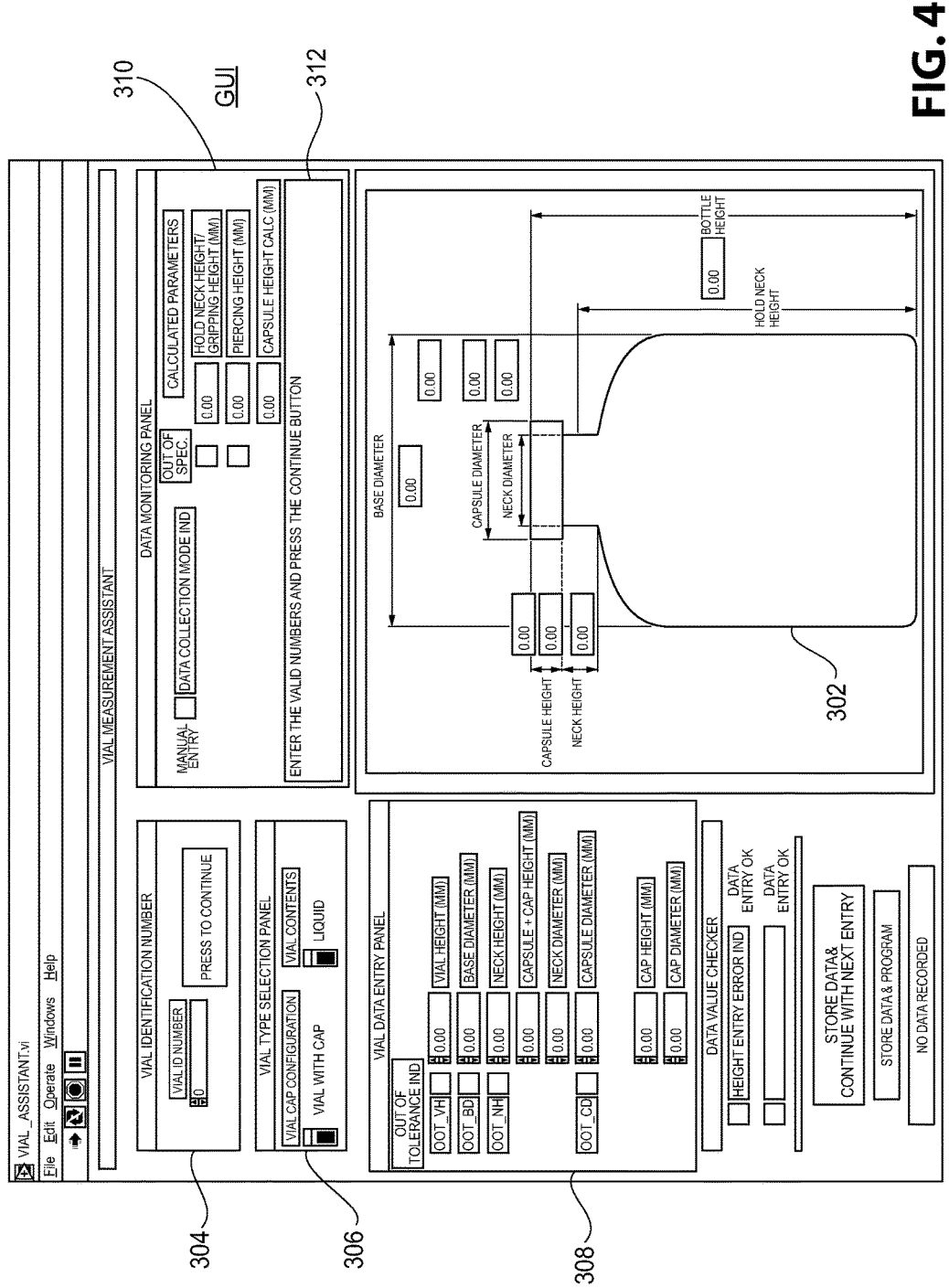
FIG. 4 is an example GUI according to an aspect of the disclosure.

The GUI provides a data entry panel 308 in which the user may input measured values for the dimensions of the medication or container 108. The GUI further displays linear dimensions of critical elements of the medication or container 108 to be measured on the representation 302. The linear dimensions may be shown as leader lines and arrows with a value box. For example, FIG. 4 shows lead lines and arrows with a value box for dimension measurements associated with the base diameter, capsule diameter, neck diameter, capsule height, neck height, and bottle height of an example container. After a dimension of the container 108 is measured with the digital caliper 102, the value is automatically loaded into and displayed in the respective value box for which the measurement has been taken and into a corresponding box in the vial data entry panel 308.

The computer 104 may check the measured values for errors. The GUI may indicate whether the measured values are correct or contain errors in the data entry panel 308. The data entry panel 308 indicates to the user if a measured value is outside of a tolerance threshold for that value. For example, the data entry panel 308 may indicate that a measured value does not satisfy a threshold for a height entry or a diameter entry. The measured values may be checked for errors by comparing the measured values to known values previously stored in the database 114 and/or to previously input measured values, which may be set as the tolerance thresholds. For example, the computer 104 may identify a vial or bottle type based on an identification number and compare the measured values to stored tolerance thresholds for that vial or bottle type in the database 114. The computer 104 may identify an error if a previously entered measured value precludes the possibility of a later input value. The previously entered measured value may be set as a dynamic tolerance threshold for the container 108 currently being measured. For example, if a bottle height of five inches is entered and a capsule height of ten inches is entered, the computer 104 may identify the capsule height as an error, because the capsule height cannot be greater than the bottle height. The computer may compare a single input value to multiple different stored or previously entered values to determine the error. For example, two or more previously entered values may be combined to determine that an input value is precluded based on their combined dimensions.

The data entry panel 308 may further provide the user with input options to store the data for the current container 108 and continue with a next entry, e.g., a next container 108, store the data and end execution of the control application 105, or to end application of the control application 105 without storing the data for the current container 108.

The GUI provides a data monitoring panel 310 in which one or more derived values may be displayed and in which the user may switch between a manual entry mode and an automatic entry mode using the digital caliper 102. The computer 104 may calculate derived values by performing calculations on the measured values, and the GUI may automatically display the derived values calculated based on the measured values in the data monitoring panel 310 as the measured values upon which the derived values are calculated are input. These calculations may otherwise prove challenging for an untrained manual user. The computer may contain various algorithms to calculate dimensions of the vial or bottle based on previously input measured values and/or values stored in the database 114. For example, if input values for the bottle height, the capsule height, and the neck height have been previously entered and/or stored in the database 114, the computer 104 may calculate the hold neck height based on the bottle height, capsule height, and the neck height, e.g., by subtracting the capsule height and half of the neck height from the bottle height.

An instruction box 312 may be provided within the data monitoring panel 310. The instruction box may provide the user with instructions related to configuring and/or setting up the digital caliper 102, operation of the control application 105, and/or placement of the digital caliper 102 on the medication or container 108 to be measured for proper recording of a particular dimension.

The GUI may guide the operator through each measurement and provide prompts to the user to make or check certain measurements. The GUI may highlight or otherwise indicate a particular dimension on the representation 302 to be measured; and, when the user has the digital caliper 102 aligned on the container 108, the operator clicks a button on the display 110, a keyboard, or the digital caliper 102 to collect the measurement with the digital caliper 102.

The calipers 102 transmit the measured values to the computer 104 via the communications interface 106. The transmitted measurements may be encoded and/or encrypted. The computer 104 receives the transmitted measured values, decodes and/or decrypts the data, performs error checking and the calculation of any derived values, populates the corresponding areas of the GUI with the measured values, and automatically stores the received measurement data in the database 114. For example, the computer 104 compares each received measured value to other collected values and/or the information on each medicine stored in the database 114. The value is decoded and stored in the database 114 and is shown on the GUI in the corresponding linear dimension box. The next measurement is then highlighted and so on until the characterization of the physical medication is complete. In addition, other important characteristics may be identified by the GUI and provided by the user through other input devices. These additional characteristics may include the form of the medication (e.g., liquid or powder; round, tablet, or capsule; etc.), the name of the medication, a barcode value input with a barcode reader, or an image input by a camera, etc.

Figure 5:
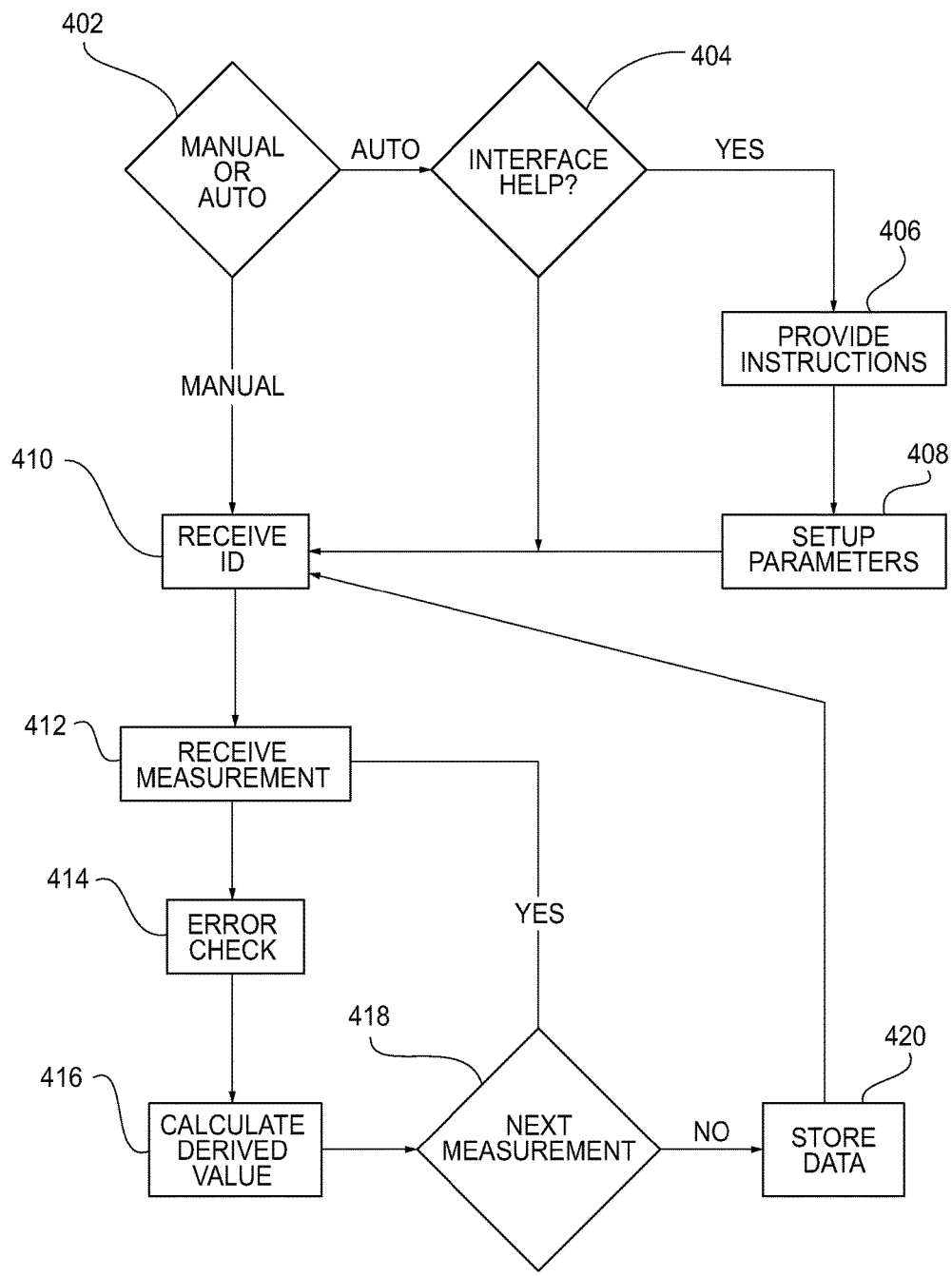
FIG. 5 is a flow chart of a method for measuring medication sizes according to an aspect of the disclosure.

FIG. 5 is a flow chart of a method for measuring medication sizes according to a preferred and non-limiting embodiment. In stage 402, the computer 104 determines whether a digital caliper 102 is configured for automatic entry of measured values or if a user will manually enter the values into the display 110 (e.g., GUI). For example, the computer 104 may automatically detect a connection of the digital caliper 102 via the communications interface 106 and/or the computer 104 may present the user an option via the display/GUI 110, e.g., in data monitoring panel 310, to select either manual entry of measured values or automatic entry of the measured values with the digital caliper 102. If, at stage 402, the computer 104 determines that automatic entry using the digital caliper 102 is selected, the computer 104 presents the user with an option via the display/GUI 110 to receive help interfacing to the digital caliper 102 at stage 404. If the user, at stage 404, selects via the display/GUI 110 to receive help with interfacing the digital caliper 102, processing proceeds to stage 406 where the user is provided with instructions via the display/GUI 110 to set up the calipers 102, e.g., in instruction box 312. For example, the instructions may include help for connecting the digital caliper 102 to the computer 104 via the communications interface 106. After the user connects the digital caliper 102 in stage 406, the computer 104 may set up the digital caliper serial interface parameters in stage 408.

After the user selects manual entry in stage 402, the user declines help interfacing the calipers 102 in stage 404, or the computer 104 sets up the digital caliper serial interface parameters in stage 408, processing proceeds to stage 410 where the display/GUI 110, as shown in FIG. 4, provides an area for the user to enter an identification number for the medication or medication container 108 to be measured, e.g., identification number area 304.

At stage 412 the display/GUI 110 displays linear dimensions of critical elements of the medication or container 108 to be measured on the representation 302, instructs the user on how to place the digital caliper 102 to measure the dimensions, e.g., in instruction box or area 312, and receives a measurement value, either via manual entry via the display/GUI 110 by the user or from the digital caliper 102 depending upon the mode of operation chosen in stage 402. At stage 414, the computer 104 checks the measured value for errors and displays via the display/GUI 110, e.g., in data entry panel 308, whether the measured values are correct or contain errors. At stage 416, the computer 104 calculates any derived values based on the input values and automatically displays the derived values calculated based on the input values in the display/GUI 110, e.g., in data monitoring panel 310. At stage 418, the user is presented via the display/GUI 110 the option to enter another measured value. If the user selects the option to enter another measured value, the processing returns to stage 412. Alternatively, the user may select the option to store the data in the database 114 at stage 420.

Disclosed embodiments may be particularly useful in IV robotics to characterize the critical parameters of a vial of medicine, and in high speed packagers to measure a solid medication directly. Disclosed embodiments may also be particularly useful in RobotRx® to measure the thickness of a medication to identify a number of medications that may fit on a rod.

As previously noted, preferred and non-limiting embodiments may be implemented on a variety of computing devices and systems, wherein these computing devices include the appropriate processing mechanisms and computer-readable media for storing and executing computer-readable instructions, such as programming instructions, code, and the like. As shown in FIG. 6, personal computers 900, 944, in a computing system environment 902 are provided. This computing system environment 902 may include, but is not limited to, at least one computer 900 having certain components for appropriate operation, execution of code, and creation and communication of data. For example, the computer 900 includes a processing unit 904 (typically referred to as a central processing unit or CPU) that serves to execute computer-based instructions received in the appropriate data form and format. Further, this processing unit 904 may be in the form of multiple processors executing code in series, in parallel, or in any other manner for appropriate implementation of the computer-based instructions.

In order to facilitate appropriate data communication and processing information between the various components of the computer 900, a system bus 906 is utilized. The system bus 906 may be any of several types of bus structures, including a memory bus or memory controller, a peripheral bus, or a local bus using any of a variety of bus architectures. In particular, the system bus 906 facilitates data and information communication between the various components (whether internal or external to the computer 900) through a variety of interfaces, as discussed hereinafter.

The computer 900 may include a variety of discrete computer-readable media components. For example, this computer-readable media may include any media that can be accessed by the computer 900, such as volatile media, non-volatile media, removable media, non-removable media, etc. As a further example, this computer-readable media may include computer storage media, such as media implemented in any method or technology for storage of information, such as computer-readable instructions, data structures, program modules, or other data, random access memory (RAM), read only memory (ROM), electrically erasable programmable read only memory (EEPROM), flash memory, or other memory technology, CD-ROM, digital versatile disks (DVDs), or other optical disk storage, magnetic cassettes, magnetic tape, magnetic disk storage, or other magnetic storage devices, or any other medium which can be used to store the desired information and which can be accessed by the computer 900. Further, this computer-readable media may include communications media, such as computer-readable instructions, data structures, program modules, or other data in a modulated data signal, such as a carrier wave or other transport mechanism and include any information delivery media, wired media (such as a wired network and a direct-wired connection), and wireless media (such as acoustic signals, radio frequency signals, optical signals, infrared signals, biometric signals, bar code signals, etc.). Of course, combinations of any of the above should also be included within the scope of computer-readable media.

The computer 900 further includes a system memory 908 with computer storage media in the form of volatile and non-volatile memory, such as ROM and RAM. A basic input/output system (BIOS) with appropriate computer-based routines assists in transferring information between components within the computer 900 and is normally stored in ROM. The RAM portion of the system memory 908 typically contains data and program modules that are immediately accessible to or presently being operated on by the processing unit 904, e.g., an operating system, application programming interfaces, application programs, program modules, program data, and other instruction-based computer-readable codes.

With continued reference to FIG. 6, the computer 900 may also include other removable or non-removable, volatile or non-volatile computer storage media products. For example, the computer 900 may include a non-removable memory interface 910 that communicates with and controls a hard disk drive 912, e.g., a non-removable, non-volatile magnetic medium; and a removable, non-volatile memory interface 914 that communicates with and controls a magnetic disk drive unit 916 (which reads from and writes to a removable, non-volatile magnetic disk 918), an optical disk drive unit 920 (which reads from and writes to a removable, non-volatile optical disk 922, such as a CD ROM), a Universal Serial Bus (USB) port 921 for use in connection with a removable memory card, etc. However, it is envisioned that other removable or non-removable, volatile or non-volatile computer storage media can be used in the exemplary computing system environment 902, including, but not limited to, magnetic tape cassettes, DVDs, digital video tape, solid state RAM, solid state ROM, etc. These various removable or non-removable, volatile or non-volatile magnetic media are in communication with the processing unit 904 and other components of the computer 900 via the system bus 906. The drives and their associated computer storage media discussed above and illustrated in FIG. 6 provide storage of operating systems, computer-readable instructions, application programs, data structures, program modules, program data, and other instruction-based computer-readable code for the computer 900 (whether duplicative or not of this information and data in the system memory 908).

A user may enter commands, information, and data into the computer 900 through certain attachable or operable input devices, such as a keyboard 924, a mouse 926, etc., via a user input interface 928. Of course, a variety of such input devices may be utilized, e.g., a microphone, a trackball, a joystick, a touchpad, a touch-screen, a scanner, etc., including any arrangement that facilitates the input of data, and information to the computer 900 from an outside source. As discussed, these and other input devices are often connected to the processing unit 904 through the user input interface 928 coupled to the system bus 906, but may be connected by other interface and bus structures, such as a parallel port, game port, or a USB. Still further, data and information can be presented or provided to a user in an intelligible form or format through certain output devices, such as a monitor 930 (to visually display this information and data in electronic form), a printer 932 (to physically display this information and data in print form), a speaker 934 (to audibly present this information and data in audible form), etc. All of these devices are in communication with the computer 900 through an output interface 936 coupled to the system bus 906. It is envisioned that any such peripheral output devices be used to provide information and data to the user.

The computer 900 may operate in a network environment 938 through the use of a communications device 940, which is integral to the computer or remote therefrom. This communications device 940 is operable by and in communication to the other components of the computer 900 through a communications interface 942. Using such an arrangement, the computer 900 may connect with or otherwise communicate with one or more remote computers, such as a remote computer 944, which may be a personal computer, a server, a router, a network personal computer, a peer device, or other common network nodes, and typically includes many or all of the components described above in connection with the computer 900. Using appropriate communication devices 940, e.g., a modem, a network interface or adapter, etc., the computer 900 may operate within and communication through a local area network (LAN) and a wide area network (WAN), but may also include other networks such as a virtual private network (VPN), an office network, an enterprise network, an intranet, the Internet, etc. It will be appreciated that the network connections shown are exemplary and other means of establishing a communications link between the computers 900, 944 may be used.

As used herein, the computer 900 includes or is operable to execute appropriate custom-designed or conventional software to perform and implement the processing steps of the method and system of the present invention, thereby forming a specialized and particular computing system. Accordingly, the presently-invented method and system may include one or more computers 900 or similar computing devices having a computer-readable storage medium capable of storing computer-readable program code or instructions that cause the processing unit 904 to execute, configure, or otherwise implement the methods, processes, and transformational data manipulations discussed hereinafter in connection with the present invention. Still further, the computer 900 may be in the form of a personal computer, a personal digital assistant, a portable computer, a laptop, a palmtop, a mobile device, a mobile telephone, a server, or any other type of computing device having the necessary processing hardware to appropriately process data to effectively implement the presently-invented computer-implemented method and system.

It will be apparent to one skilled in the relevant art(s) that the system may utilize databases physically located on one or more computers which may or may not be the same as their respective servers. For example, programming software on computer 900 can control a database physically stored on a separate processor of the network or otherwise.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system for measuring medication, the system comprising:
    at least one non-transitory computer-readable storage medium in communication with one or more processors and having instructions stored thereon which, when executed by the one or more processors, cause the one or more processors to perform operations comprising:
    providing a graphical user interface (GUI) including a representation of a medication or a medication container;
    providing in the GUI an indication to measure at least one dimension of the medication or the medication container;
    receiving at least one signal comprising at least one measured dimension of the medication or the medication container;
    processing the at least one measured dimension;
    storing the at least one measured dimension;
    providing the at least one measured dimension in the GUI in association with the indication to measure the at least one dimension of the medication or the medication container;
    dynamically setting at least one dynamic tolerance threshold based at least partly on at least one previously measured dimension of the medication or the medication container currently being measured; and
    automatically providing a prompt in the GUI to check the at least one measured dimension based on the at least one dynamic tolerance threshold, wherein the prompt indicates the at least one dimension in the representation of the medication or the medication container.

2. The system of claim 1, wherein the indication to measure the at least one dimension of the medication or the medication container comprises at least one marking in the GUI indicating the dimension on the representation of the medication or the medication container.

3. The system of claim 2, wherein the at least one marking in the GUI comprises at least one lead line and at least one arrow.

4. The system of claim 1, wherein the processing the at least one measured dimension comprises determining that the measured dimension fails to satisfy the at least one dynamic tolerance threshold.

5. The system of claim 1, wherein the processing the at least one measured dimension comprises calculating a derived value based at least partly on the at least one measured dimension, and wherein the derived value is another dimension of the medication or the medication container.

6. The system of claim 1, wherein the one or more processors perform operations comprising:
    receiving information indicating a type of the medication or the medication container.

7. The system of claim 6, wherein the representation is based at least partly on the information indicating the type of the medication or the medication container.

8. The system of claim 6, wherein the receiving the information comprises at least one of scanning a barcode on the medication or the medication container and capturing an image of the medication or the medication container.

9. The system of claim 7, further comprising:
    a digital caliper configured to electronically measure the at least one measured dimension and transmit the at least one measured dimension to the one or more processors via a communications interface, wherein the medication or medication container includes the medication container, wherein the prompt includes an instruction on how to place the digital caliper on the medication container to measure the at least one dimension, and wherein the instruction is based at least partly on the type of the medication container.

10. A method for measuring medication, the method comprising:
    providing, by one or more processors, a graphical user interface (GUI) including a representation of a medication or a medication container;
    providing, by the one or more processors, in the GUI an indication to measure at least one dimension of the medication or the medication container;
    receiving, by the one or more processors, at least one signal comprising at least one measured dimension of the medication or the medication container;
    processing, by the one or more processors, the at least one measured dimension;
    storing, by the one or more processors, the at least one measured dimension; and
    providing, by the one or more processors, the at least one measured dimension in the GUI in association with the indication to measure the at least one dimension of the medication or the medication container; and
    dynamically setting, by the one or more processors, at least one dynamic tolerance threshold based at least partly on at least one previously measured dimension of the medication or the medication container currently being measured; and
    automatically providing, by the one or more processors, a prompt in the GUI to check the at least one measured dimension based on the at least one dynamic tolerance threshold, wherein the prompt indicates the at least one dimension in the representation of the medication or the medication container.

11. The method of claim 10, wherein the indication to measure the at least one dimension of the medication or the medication container comprises at least one marking in the GUI indicating the dimension on the representation of the medication or the medication container.

12. The method of claim 11, wherein the at least one marking in the GUI comprises at least one leader line and at least one arrow.

13. The method of claim 10, wherein the processing the at least one measured dimension comprises determining that the measured dimension fails to satisfy the at least one dynamic tolerance threshold.

14. The method of claim 10, wherein the processing the at least one measured dimension comprises calculating a derived value based at least partly on the at least one measured dimension, and wherein the derived value is another dimension of the medication or the medication container.

15. The method of claim 10, further comprising:
receiving, by the one or more processors, information indicating a type of the medication or the medication container.

16. The method of claim 15, wherein the representation is based at least partly on the information indicating the type of the medication or the medication container.

17. The method of claim 16, further comprising:
measuring, by a digital caliper, the at least one measured dimension, wherein the medication or medication container includes the medication container, wherein the prompt includes an instruction on how to place the digital caliper on the medication container to measure the at least one dimension, and wherein the instruction is based at least partly on the type of the medication container; and transmitting, by the digital caliper, the at least one measured dimension to the one or more processors via a communications interface.

18. The method of claim 15, wherein the receiving the information comprises at least one of scanning a barcode on the medication or the medication container and capturing an image of the medication or the medication container.

* * * * *